United States Patent [19]

Burba et al.

[11] Patent Number: 4,968,767

[45] Date of Patent: Nov. 6, 1990

[54] SUBSTITUTED 3-(N-IMIDAZOLYL)PROPIONIC HYDRAZIDES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING THEM

[75] Inventors: Christian Burba, Herbern; Werner Mrotzek, Dortmund, both of Fed. Rep. of Germany

[73] Assignee: Schering AG, Berlin and Bergkamen, Fed. Rep. of Germany

[21] Appl. No.: 365,829

[22] Filed: Jun. 14, 1989

[30] Foreign Application Priority Data

Jul. 7, 1988 [DE] Fed. Rep. of Germany ....... 3822959

[51] Int. Cl.$^5$ ................ C08G 59/54; C07D 233/61
[52] U.S. Cl. .................................. 528/94; 528/117; 528/361; 528/367; 528/407; 528/408; 528/365; 252/182.18; 252/182.28; 548/341
[58] Field of Search ............... 548/341; 528/117, 367, 528/408, 94, 361, 407; 252/182.28, 182.18

[56] References Cited

U.S. PATENT DOCUMENTS

| | | | |
|---|---|---|---|
| 2,966,478 | 12/1960 | Harrison | 528/117 |
| 2,994,685 | 8/1961 | Delmonte et al. | 528/407 |
| 3,792,016 | 2/1974 | Hill et al. | 528/407 |
| 3,912,689 | 10/1975 | Bechara et al. | 528/407 |

FOREIGN PATENT DOCUMENTS 0106635 4/1984 European Pat. Off. .

OTHER PUBLICATIONS

Lee, H., et al., Handbook of Epoxy Resins, McGraw Hill, New York, 1967, pp. 22-10 to 22-21.

Primary Examiner—Mary C. Lee
Assistant Examiner—Lenora Mittenberger
Attorney, Agent, or Firm—Curtis, Morris & Safford

[57] ABSTRACT

The invention relates to substituted 3-(N-imidazolyl)-propionic hydrazides, to their use as curing agents in epoxy-resin compositions, and to curable epoxy-resin compositions containing them and comprised of (a) an epoxy resin, and (b) optionally of dicyandiamide, and (c) optionally of conventionally used nitrogen-containing heterocyclic amine compounds, for the production of molded articles.

20 Claims, No Drawings

SUBSTITUTED 3-(N-IMIDAZOLYL)PROPIONIC HYDRAZIDES, THEIR USE AS CURING AGENTS IN EPOXY-RESIN COMPOSITIONS, AND CURABLE EPOXY-RESIN COMPOSITIONS AND MOLDED EPOXY-RESIN ARTICLES INCORPORATING THEM

This invention relates to substituted 3-(N-imidazolyl)-propionic hydrazides, their use as curing agents in epoxy-resin compositions, and curable epoxy-resin compositions containing them and comprised of (a) an epoxy resin, (b) optionally dicyandiamide, and (c) optionally commonly used nitrogen-containing heterocyclic amine compounds, for the production of molded articles.

For the manufacture of composite materials, two basic processes are employed today. One of these is the wet-in-wet process in which the reinforcing materials are impregnated with the curable mixture, superimposed on one another in the wet state while being shaped, and heat-cured in one step to the thermoset final state.

In the other process, the two-step process, so-called prepregs are first produced from the reinforcing materials and the curable mixture, and these prepregs are then processed to the finished parts in a separate second step. With respect to operating procedure, a distinction is made between working with solvents and working without solvents.

The prepregs are normally produced in a continuous process in which the reinforcing materials are conducted through an impregnating bath of the resin/curing agent mixture being used, or the impregnant is mixed only just before it is applied to the reinforcing materials and then knife-coated onto the latter with a special device. The amount of impregnant to be applied to a given reinforcement web is controlled not only through the viscosity of the impregnant but also by means of squeeze rolls downstream of the point of application.

In the case of solvent systems, the solvent contained in the impregnating solution is evaporated through the addition of heat after the impregnating operation, and the resin system is at the same time converted from the A stage to the B stage. The reinforcing material impregnated with impregnants which range from fluid to strongly viscid is thus turned into a slightly tacky to almost dry prepreg, depending on the operating conditions and on the resin system used. It is important in this process step that on the one hand the solvent be completely eliminated from the impregnating mixture and that on the other hand the latent curing agent required for curing the prepreg in the second process step not be activated as yet so that the reaction which the impregnated reinforcing material undergoes does not prematurely go to completion.

With solvent-free systems, impregnation is also followed by a short heat treatment of the material to convert the impregnant to the B stage, or, depending on the chemical composition of the resin system, the reinforcing materials are lined on both sides with release sheets directly after impregnation, without a special heat treatment, and placed into appropriate interim storage. In the course of such storage, the resin system is gradually converted to the B stage, or then the impregnant is bonded to the reinforcing materials through physical effects alone, chemical changes being largely dispensed with.

The prepregs so obtained can be stored temporarily and transported as rolls before they are cut to size and stacked to component thickness as required by their intended end use. Through the simultaneous action of pressure and temperature, the prepreg stack is then cured completely to give a high-strength molded article, with the still low-molecular-weight, flowable resins being converted to the high-molecular-weight C stage of a thermoset.

While in the one-step process long open times and short cure times at low cure temperatures are required, an additional requirement in the two-step process is that the prepreg possess storage stability for a maximum length of time. Storage temperatures lower than room temperature have become steadily less acceptable in practice.

Of importance is, moreover, that depending on the prepreg manufacturing method the material viscosity of the ready-to-use curable mixture remain substantially constant for as long a period of time as possible. This is necessary in order to achieve constant resin deposition and a constant B stage especially when an impregnating bath of large volume is used, since on the one hand the manufacturing conditions cannot be continuously adjusted to the changing relationships in the curable mixture and on the other hand the physical properties of the fully cured end product are adversely affected thereby.

In practice, it is desired to obtain a curable mixture whose viscosity remains constant in the impregnating bath even for an extended period of time, which reacts at low temperature in a short time to the B stage, and which can then be stored as a prepreg at room temperature for a long period of time without undergoing chemical changes.

Independently of prepreg manufacture, the mixture should cure completely within a short time at as low a temperature as possible, the maximum temperature of the exothermic reaction should remain at a low level even with appreciable layer thicknesses, and the physical properties of the end product should be on a level that meets practical requirements, meaning in particular that the glass-transition temperatures determined by the matrix should be higher than 140° C. These requirements involving curing behavior and property level also apply to epoxy-resin systems to be processed by the wet-in-wet process.

Dicyandiamide, long used as a curing agent in curable mixtures based on epoxy resins, is usually combined with co-curing agents and/or accelerators to achieve the desired properties. A great many suggestions for its use in this field are therefore known from the literature.

While the concurrent use of tertiary amines such as benzyldimethylamine, tertiary/secondary amines such as 2-methylimidazole or 2-ethyl-4-methylimidazole, and tertiary/primary amines such as 1-aminoethylimidazole, alone or in mixtures, has gradually brought about improvements, it has fallen short of remedying serious shortcomings.

In the literature, it has further been proposed to use, in addition to dicyandiamide, dihydrazides of dicarboxylic acid as latent curing agents for epoxy resins.

However, these hydrazides have the drawback that the temperature at which the curing reaction is initiated occasionally is quite high and that a complete cure can be obtained only by the use of temperatures of about 150° C. and higher over a long period of time.

From European Pat. No. 106,635, hydrazides are known which are produced by the addition of acrylic esters to straight-chain aliphatic polyfunctional amines and subsequent reaction with hydrazine hydrate to give the corresponding polyfunctional hydrazides. However, user demands for activation temperatures of about 100° C. coupled with the lowest possible peak exotherms, short cure times, and glass-transition temperatures of 140° C. or higher are not satisfied by these products, either.

The present invention has as its object to provide curable mixtures based on epoxy compounds and latent curing agents which overcome the drawbacks of the prior art, fully cure within a short time at relatively low temperatures and without high peak exotherms to the thermoset final state, possess a thermal stability meeting practical requirements, and in prepregs have adequate storage stability at room temperature.

Said object is accomplished by the use of a novel curing agent, optionally with the concurrent use of conventionally used latent curing agents.

One embodiment of the invention thus are compounds of the general formula

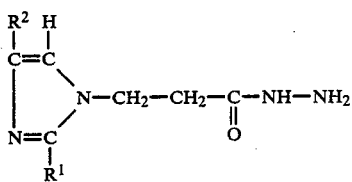

wherein $R^1$ and $R^2$ may, independently of each other, have the meaning of H, —CH$_3$, —C$_2$H$_5$ or phenyl.

Another embodiment of the invention is the use of compounds of the general formula

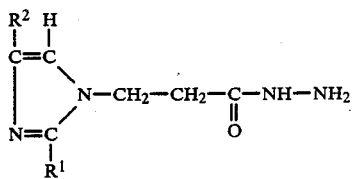

wherein $R^1$ and $R^2$ may, independently of each other, have the meaning of H, —CH$_3$, —C$_2$H$_5$ or phenyl, optionally with the concurrent use of conventionally used nitrogen-containing heterocyclic amine compounds as curing agents for epoxy resins.

A further embodiment of the invention are curable epoxy-resin compositions containing
(a) an epoxy resin having on the average more than one epoxy group per molecule, and optionally
(b) dicyandiamide, and optionally
(c) solvents, fillers, reinforcements or embedments, pigments and auxiliaries, and
(d) compounds of the general formula

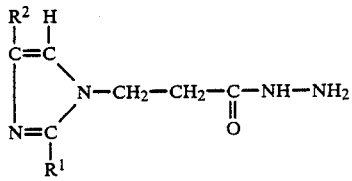

wherein $R^1$ and $R^2$ may, independently of each other, have the meaning of H, —CH$_3$, —C$_2$H$_5$ or phenyl, and optionally
(e) conventionally used nitrogen-containing heterocyclic amine compounds.

Still another embodiment of the invention are curable epoxy-resin compositions wherein the reinforcements or embedments are impregnated at room temperature with a binder comprised of
(a) an epoxy resin having on the average more than one epoxy group per molecule, and optionally
(b) dicyandiamide, and optionally
(c) solvents, fillers, reinforcements or embedments, pigments and auxiliaries, and
(d) compounds of the general formula

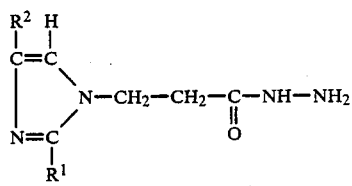

wherein $R^1$ and $R^2$ may, independently of each other, have the meaning of H, —CH$_3$, —C$_2$H$_5$ or phenyl, and optionally
(e) conventionally used nitrogen-containing heterocyclic amine compounds
and optionally converted at elevated temperature to the semisolid but still fusible state (B stage).

A further embodiment of the invention are molded epoxy-resin articles which are characterized in that in a first step the reinforcements or embedments are impregnated at room temperature with a binder comprised of
(a) an epoxy resin having on the average more than one epoxy group per molecule, and optionally
(b) dicyandiamide, and optionally
(c) solvents, fillers, reinforcements or embedments, pigments and auxiliaries, and
(d) compounds of the general formula

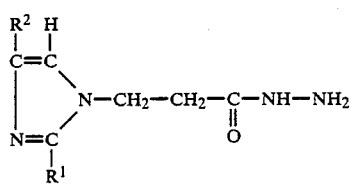

wherein $R^1$ and $R^2$ may, independently of each other, have the meaning of H, —CH$_3$, —C$_2$H$_3$ or phenyl, and optionally
(e) conventionally used nitrogen-containing heterocyclic amine compounds
and optionally converted to the semisolid but still fusible state (B stage) and in a second step the wet laminates or prepregs, alone and with shaping, or placed between substrates to be bonded, are cured completely at elevated temperature and under pressure.

The epoxy resins used concurrently in accordance with the invention are glycidyl esters and ethers with two or more epoxy groups per molecule, such as preferably the glycidyl ethers based on mono- or polyhydric phenols. Preferred are, in accordance with the invention, glycidyl ethers of 2,2-bis(4-hydroxyphenyl)propane (bisphenol A) with epoxy values of from 0.2 to 0.6, and particularly the compounds which are liquid at room temperature and have epoxy values of about 0.45 to 0.55. The glycidyl ethers based on bisphenol F and the novolacs have also proved advantageous.

Dicyandiamide, optionally used concurrently as a curing agent, is a commercial product that is available under known trade names. The amount of dicyandiamide will range from 2 to 10 parts by weight, depending on the epoxy compound used, and in the case of the bisphenol A-based liquid glycidyl ethers preferred in accordance with the invention from 5 to 10 parts by weight, based on 100 parts by weight of diglycidyl ether.

The curing agents or accelerators used in accordance with the invention are compounds of the general formula

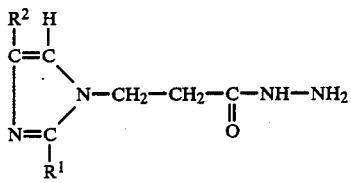
(I)

The amount of curing agent or accelerator may vary over a wide range. It is determined by the intended end use and the curing conditions which the latter may require. In accordance with the invention, amounts ranging from 0.1 to 40 parts by weight, and preferably from 1 to 10 parts by weight, based on 100 parts by weight of epoxy compound, are used.

Suitable for concurrent use as conventionally used nitrogen containing heterocyclic amine compounds are N-alkylimidazoles such as N-methylimidazole, N-ethylimidazole and/or imidazoline compounds of the general formula

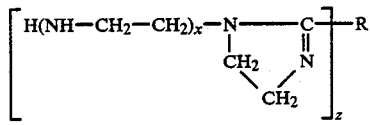
(II)

wherein R is an optionally branched alkyl or alkylene group having fewer than 10 carbon atoms, and particularly $-CH_3$, $-CH(OH)-CH_3$, $-(CHR')_y$; wherein R' is H or $-CH_3$, x is 1, 2 or 3, y is from 4 to 8, and z is equal to the valence of R, and particularly those wherein x is 1, z is 1, and R is $-CH_3$ or $-CH_2-CH_3$.

For modification of the properties of the end product, modifiers or auxiliaries, such as phenolic resins, melamine resins or silicone resins, inorganic and organic fillers such as quartz powders, titanium dioxide, carbon black, silicone rubber or butadiene rubber, may be used concurrently, in addition to other epoxy resins.

To obtain the desired viscosity, resins of different viscosities or diluents may be used, as may the usual solvents, such as dimethyl formamide, acetone, methyl ethyl ketone, methyl glycol and propylene glycol monomethyl ether or mixtures thereof.

For making the prepregs, organic and inorganic fibers, nonwoven and woven fabrics based on aramid, carbon or cellulose, metals such as boron, steel, etc., ceramics, and especially glass may be used.

The solvent-containing prepregs are produced by a method which is known per se and in which the reinforcing materials are impregnated with the reactive resin mixture in an impregnating bath and, after the excess resin has been squeezed off, are converted continuously, with addition of energy (mostly heat) and simultaneous elimination of the solvent, from the A stage to the B stage. Depending on the desired consistency of the prepregs (viscid to solid), these are then provided on both sides with a release sheet and wound into a roll for storage and transportation. Further processing involves cutting the individual prepreg layers to size and assembling them into a stack, from which a highly crosslinked part is produced by shaping measures with the simultaneous addition of heat.

The inventive curing agents may also be used successfully in solventless systems based on epoxy resins and optionally dicyandiamide. Examples are solventless prepregs, with or without dicyandiamide, having storage stability, wet laminates, heat-curing one-component adhesives for the bonding of body parts in the automobile industry (flange-joint adhesives), and epoxy-resin castings, epoxy-resin coating compositions or epoxy-resin filament- or tape-wound structures.

EXAMPLES

I Preparation of an inventive curing agent or accelerator from 2-ethyl-4-methylimidazole (EMI-2,4), methyl acrylate and hydrazine 55 g of EMI-2,4 (0.5 mol) in 55 ml of methanol is introduced as initial charge with stirring at 50° C. To this solution there is slowly added dropwise 43 g of methyl acrylate (0.5 mol) and the mixture is allowed to react further for 1 hr. at 50° C. This reaction mixture is slowly added dropwise to a solution, preheated to 70° C., of 31.3 g of hydrazine hydrate, 80% (0.5 mol hydrazine), in 50 ml of methanol. The mixture is allowed to react further for 3 hr. at 70° C. and the completion of hydrazide formation (disappearance of ester band) is monitored in the IR spectrum.

After elimination of the methanol in a rotary evaporator, a viscous, yellowish liquid tending to crystallize is obtained, which can be used as a accelerator without further purification.

I (a) Preparation of a prepreg reaction mixture from I with the concurrent use of dicyandiamide A solution of 16 g of dicyandiamide and 3 g of the reaction product I in 101 g of reagent-grade dimethyl formamide, prepared at room temperature, is mixed with 60 phr of an epoxy resin (epoxide equivalent approximately 190) and used to produce prepregs.

The prepregs are produced on the laboratory scale by coating the impregnating solution onto a satin-weave glass-filament fabric (296 g/m²) measuring approximately 0.1 m² which after impregnation is heat-treated for 5 minutes at 100° C. in a forced-air oven. After the solvent has been evaporated and the resin system converted from the A stage to the B stage, flexible, slightly tacky prepregs are obtained which even after several weeks storage between polyethylene sheets at room temperature can be processed to highstrength molded articles.

For determination of the glass-transition temperature of the completely reacted resin/curing agent mixture, the prepreg layers produced as described above were molded by the hot-press method for 30 minutes at 120° C. and 0.1 bar. The end product, fully cured in this manner, exhibits no flaws of any kind with regard to the adhesion of the individual prepreg layers to one another and, as shown in Table 1, has a glass-transition temperature of 148° C.

The viscosities of the impregnating solutions, also given in that table, were determined by means of a cone-plate rheometer made by Epprecht Instruments, the solutions being kept in a closed container at room temperature between the individual measurements.

Also shown in that table are the activation temperatures of the impregnating solutions and the peak temperatures obtained when the maximum exotherm was exceeded, determined by means of a TA 3000 differential scanning calorimetry (DSC) unit with a DSC 30 measuring cell, manufactured by Mettler, with a starting temperature of 20° C. and heating rates of 10° and 20° C./minute.

I (b) Preparation of a prepreg reaction mixture from I with the concurrent use of dicyandiamide A solution of 16 g of dicyandiamide and 6 g of reaction product I in 98 g of reagent-grade dimethyl formamide, prepared at room temperature, is mixed with 60 phr of an epoxy resin (epoxide equivalent approximately 190) and used to produce, by the method described in Example I (a), prepregs storable at room temperature and high-strength end products. The features which are characteristic of this example are presented in Table 1 as for Example I (a).

II Preparation of a noninventive accelerator from 1,12-diaminododecane, methyl acrylate and hydrazine hydrate In accordance with European Pat. No. 106,635, example 4, the reaction product of 1,12-diaminododecane, methyl acrylate and hydrazine hydrate is obtained in crystalline form.

II (a) Preparation of a prepreg reaction mixture from II with the concurrent use of dicyandiamide 101 g of reagent-grade dimethyl formamide is first heated to 80° C., because of the poor solubility of reaction product II in this solvent, and then mixed with 3 g of reaction product II and 16 g of dicyandiamide. This solution is mixed with 60 phr of an epoxy resin (epoxide equivalent approximately 190) and, after cooling to room temperature, used to produce prepregs.

The prepregs are produced and processed further in the manner described in Example I (a). However, at a molding temperature of 120° C., the end product still is cured only so weakly that even when the molding time is tripled from 30 to 90 minutes the glass-transition temperatures cannot be determined on this product by the torsional-vibration testing method. The further characteristics of this example are also given in Table 1 for comparison.

II (b) Preparation of a prepreg reaction mixture from II with the concurrent use of dicyandiamide A solution of 16 g of dicyandiamide and 6 g of reaction product II in 98 g of reagent-grade dimethyl formamide, prepared as in II (a), is mixed with 60 phr of an epoxy resin (epoxide equivalent approximately 190) and used as in Example II (a) to produce prepregs. With respect to properties, see Table 1.

III Use of a noninventive N-substituted imidazole derivative, N-methylimidazole, as an accelerator in combination with dicyandiamide III (a) Preparation of a prepreg reaction mixture from N-methylimidazole with the concurrent use of dicyandiamide A solution of 16 g of dicyandiamide and 3 g of N-methylimidazole in 101 g of reagent-grade dimethyl formamide is mixed with 60 phr of an epoxy resin (epoxide equivalent approximately 190) and used as in Example I (a) to produce prepregs.

With respect to properties, see Table 1.

III (b) Preparation of a pregreg reaction mixture from N-methylimidazole with the concurrent use of dicyandiamide A solution of 16 g of dicyandiamide and 6 g of N-methylimidazole in 98 g of reagent-grade dimethyl formamide is mixed with 60 phr of an epoxy resin (epoxide equivalent approximately 190) and used as in Example I (a) to produce prepregs.

With respect to properties, see Table 1.

IV Preparation of a prepreg reaction mixture from I without the concurrent use of dicyandiamide and without a solvent 100 g of an epoxy resin (epoxide equivalent approximately 190) is mixed at room temperature with 5 g of the inventive reaction product I and used to produce prepregs. This mixture has a viscosity of 19.5 Pa·s at room temperature and can still be processed after 10 hours.

The prepregs are produced on the laboratory scale by coating the reaction mixture onto a satin-weave glass-filament fabric measuring approximately 0.1 m², which after impregnation is lined on both sides with release sheets and stored at room temperature.

After 24 hours storage at room temperature, the material has matured sufficiently to be processed further as a slightly tacky prepreg in several layers by the hot-press molding method at 0.1 bar and temperatures of from 110° to 120° C. in from 30 minutes to 1 hour to high-strength molded articles. The end product, fully cured in this manner, exhibits no flaws of any kind with regard to the adhesion of the individual prepreg layers and has a glass-transition temperature, as determined by the torsional-vibration test in conformity with DIN 53445, of over 170° C., as shown in Table 2. The other data presented in Table 2 were obtained in the manner described in Example I (a).

The prepregs can be completely cured in accordance with the processing conditions described above even after 8 days at room temperature without any loss in their properties (Table 2), and storage at 6° C., for example, in a refrigerator will permit this period to be extended to several weeks. Moreover, even after 10 days exposure to both a temperature of 70° C. and 75% relative humidity, the fully cured materials do not exhibit the deterioration of the glass-transition temperature encountered with most other epoxy systems.

V Preparation of a prepreg reaction mixture from a noninventive N-substituted imidazole derivative, N-methylimidazole, without the concurrent use of dicyandiamide and without a solvent 100 g of an epoxy resin (epoxide equivalent approximately 190) is mixed at room temperature with 5 g of N-methylimidazole and used as in Example IV to produce prepregs.

With respect to properties, see Table 2.

TABLE 1

| Example | Viscosity of impregnating solution, in mPa·s, after preparation | 1 day | (days) | DSC heating rate 10° C./min. Activation temperature °C. | Peak temperature °C. | DSC heating rate 20° C./min. Activation temperature °C. | Peak temperature °C. | Glass-transition temperature Tg (DIN 53445) after 30-min. cure at 120° C. °C. |
|---|---|---|---|---|---|---|---|---|
| I (a)   | 70 | 70  | (8) 90  | 125 | 156 | 137 | 173 | 148 |
| II (a)  | 70 | 70  | (6) 80  | 135 | 183 | 155 | 203 | Not fully cured |
| III (a) | 60 | 90  | (2) 130 | 70  | 126 | 105 | 157 | 133 |
| I (b)   | 80 | 80  | (6) 180 | 111 | 149 | 122 | 165 | 148 |
| II (b)  | 70 | 80  | (6) 100 | 135 | 183 | 150 | 200 | Not fully cured* |
| III (b) | 70 | 160 | (2) 520 | 85  | 144 | 95  | 160 | 128 |

*Tg = 138° C. after a 90-minute cure at 120° C. plus a 60-minute cure at 150° C.

TABLE 2

| Example | DSC heating rate 10° C./min. Activation temperature °C. | Peak temperature °C. | Storage time at room temperature, days | Curing conditions | Glass-transition temperature (DIN 53445) °C. | Glass-transition temperature after 10 days storage at 70° C. and 75% relative humidity °C. |
|---|---|---|---|---|---|---|
| IV | 70 | 143 | 1 | 30 min./90° C. | 171 | |
|    |    |     | 1 | 1 hr./120° C.  | 174 | |
|    |    |     | 4 | 1 hr./120° C.  | 173 | 173 |
|    |    |     | 8 | 1 hr./120° C.  | 173 | |
| V  | 65 | 128 | 1 | 30 min./90° C. | 151 | |
|    |    |     | 4 | 1 hr./120° C.  | 150 | 150 |
|    |    |     | 8 | 1 hr./120° C.  | 150 | |

What is claimed is:

1. A compound of the formula (I)

$$\begin{array}{c} R^2 \; H \\ | \;\;\; | \\ C=C \\ | \;\;\;\;\;\;\; \diagdown \\ \;\;\;\;\;\;\;\;\;\;\; N-CH_2-CH_2-\underset{\underset{O}{\|}}{C}-NH-NH_2 \\ | \;\;\;\;\;\;\; \diagup \\ N=C \\ | \\ R^1 \end{array} \quad (I)$$

wherein $R^1$ and $R^2$ are, independently of each other, H, $-CH_3$, $-C_2H_5$ or phenyl.

2. A curing agent for an epoxy-resin composition, which agent comprises a compound as claimed in claim 1 and a N-alkylimidazole and/or a imidazoline compound of the formula (II)

$$\left[ H(NH-CH_2-CH_2)_x - N \underset{\underset{\diagdown \; CH_2 \diagup}{CH_2 \;\;\; N}}{\overset{\displaystyle\text{———}\;C}{\text{———}}} R \right]_z \quad (II)$$

wherein R is an unbranched or branched alkyl or alkylene group having fewer than 10 carbon atoms, x is 1, 2 or 3, and z is equal to the valence of R.

3. A curing agent according to claim 2, wherein the N-alkylimidazole is N-methylimidazole or N-ethylimidazole.

4. A curing agent according to claim 2, wherein in the imidazoline compound of the formula (II) R is $-CH_3$, $-CH(OH)-CH_3$ or $-(CHR')_y$ wherein R' is H or $-CH_3$ and y is from 4 to 8.

5. A curing agent according to claim 2, wherein in the imidazoline compound of the formula (II) x is 1, z is 1 and R is $-CH_3$ or $-CH_2-CH_3$.

6. A curable epoxy-resin composition comprising
 (a) an epoxy resin having on the average more than one epoxy group per molecule, and
 (b) a compound of the formula (I)

$$\begin{array}{c} R^2 \; H \\ | \;\;\; | \\ C=C \\ | \;\;\;\;\;\;\; \diagdown \\ \;\;\;\;\;\;\;\;\;\;\; N-CH_2-CH_2-\underset{\underset{O}{\|}}{C}-NH-NH_2 \\ | \;\;\;\;\;\;\; \diagup \\ N=C \\ | \\ R^1 \end{array} \quad (I)$$

wherein $R^1$ and $R^2$ are, independently of each other, H, $-CH_3$, $-C_2H_5$ or phenyl.

7. A curable epoxy-resin composition according to claim 6, further comprising dicyandiamide.

8. A curable epoxy-resin composition according to claim 6, further comprising solvents, fillers, reinforcements or embedments, pigments or auxiliaries.

9. A curable epoxy-resin composition according to claim 6, further comprising a N-alkylimidazole and/or a imidazoline compound of the formula (II)

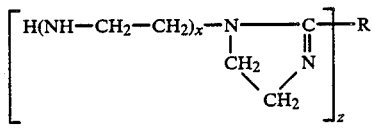

(II)

wherein R is an unbranched or branched alkyl or alkylene group having fewer than 10 carbon atoms, x is 1, 2 or 3, and z is equal to the valence of R.

10. A curable epoxy-resin composition according to claim 9, wherein the N-alkylimidazole is N-methylimidazole or N-ethylimidazole.

11. A curable epoxy-resin composition according to claim 9, wherein in the imidazoline compound of the formula (II) R is —CH$_3$, —CH(OH)—CH$_3$ or —(CHR')$_y$ wherein R' is H or —CH$_3$ and y is from 4 to 8.

12. A curable epoxy-resin composition according to claim 9, wherein in the imidazoline compound of the formula (II) x is 1, z is 1 and R is —CH$_3$ or —CH$_2$—CH$_3$.

13. A curable, epoxy-resin composition comprising a reinforcement or embedment impregnated with a binder containing
(a) an epoxy resin having on the average more than one epoxy group per molecule, and
(b) a compound of the formula (I)

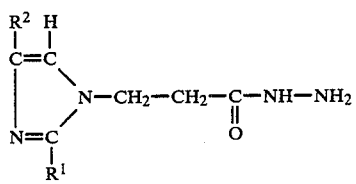

(I)

wherein R$^1$ and R$^2$ are, independently of each other, H, —CH$_3$, —C$_2$H$_5$ or phenyl.

14. A curable epoxy-resin composition according to claim 13, wherein the binder further contains dicyandiamide.

15. A curable epoxy-resin composition according to claim 13, wherein the binder further contains solvents, fillers, pigments or auxiliaries.

16. An epoxy-resin composition according to claim 13 that is converted at elevated temperature to a semisolid but fusible state (B stage).

17. A curable epoxy-resin composition according to claim 13, wherein the binder further contains a N-alkylimidazole and/or a imidazoline compound of the formula (II)

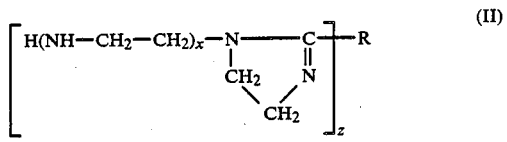

(II)

wherein R is an unbranched or branched alkyl or alkylene group having fewer than 10 carbon atoms, x is 1, 2 or 3, and z is equal to the valence of R.

18. A curable epoxy-resin composition according to claim 17, wherein the N-alkylimidazole is N-methylimidazole or N-ethylimidazole.

19. A curable epoxy-resin composition according to claim 17, wherein in the imidazoline compound of the formula (II) R is —CH$_3$, —CH(OH)—CH$_3$ or —(CHR')$_y$ wherein R' is H or —CH$_3$ and y is from 4 to 8.

20. A curable epoxy-resin composition according to claim 17, wherein in the imidazoline compound of the formula (II) x is 1, z is 1 and R is —CH$_3$ or —CH$_2$—CH$_3$.

* * * * *